United States Patent [19]

Rashtchian et al.

[11] Patent Number: 5,334,515
[45] Date of Patent: Aug. 2, 1994

[54] METHOD FOR ALTERING A NUCLEOTIDE SEQUENCE

[75] Inventors: Ayoub Rashtchian, Gaithersburg; David M. Schuster, Poolesville; George W. Buchman, III, Mt. Airy, all of Md.

[73] Assignee: Life Technologies, Inc., Gaithersburg, Md.

[21] Appl. No.: 38,071

[22] Filed: Mar. 29, 1993

Related U.S. Application Data

[63] Continuation of Ser. No. 683,684, Apr. 10, 1991, abandoned.

[51] Int. Cl.$^5$ .................. C07H 21/04; C12N 15/10; C12N 15/11; C12P 19/34
[52] U.S. Cl. ................ 435/91.2; 435/91.41; 435/91.51; 435/172.3; 435/227
[58] Field of Search .............. 435/6, 91, 172.3, 320.1, 435/91.2, 91.41, 91.51, 227; 536/24.1, 24.33, 25.3; 935/2, 8, 16, 77, 78

[56] References Cited

U.S. PATENT DOCUMENTS 4,683,202 7/1987 Mullis ........................... 435/91
4,873,192 10/1989 Kunkel ........................ 435/172.3
5,130,238 7/1992 Malek et al. ..................... 435/91

FOREIGN PATENT DOCUMENTS 329822 8/1989 European Pat. Off. .

OTHER PUBLICATIONS

Duncan, B., The Enzymes XIV:565–586 (1981).
Longo, M. C. et al., *Gene* 93:125–128 (1990).
Frohman, M. A. et al., *Proc. Natl. Acad. Sci.* (U.S.A.) 85:8998–9002 (1988).
Ohara, O. et al., *Proc. Natl. Acad. Sci.* (U.S.A.) 86:5673–5677 (1989).
Sambrook, J. et al. *Molecular Cloning: A Laboratory Manual,* 2nd ed. (1989) p. 14.6.

*Primary Examiner*—Robert A. Wax
*Assistant Examiner*—Dian C. Jacobson
*Attorney, Agent, or Firm*—Howrey & Simon

[57] ABSTRACT

A method and kit, employing exo-sample nucleotides such as deoxyuridine, capable of altering the nucleic acid sequence present at the 3' or 5' end of a DNA or RNA molecule is provided. The method and kit can be used to achieve the selective amplification of nucleic acid molecules.

16 Claims, 9 Drawing Sheets

METHOD FOR ALTERING A NUCLEOTIDE SEQUENCE

This is a continuation of application Ser. No. 683,684, filed Apr. 10, 1991, now abandoned.

FIELD OF THE INVENTION

The invention relates to improved methods for manipulating recombinant DNA in gene cloning and expression. More specifically, the invention provides methods capable of altering a nucleic acid sequence of a target sequence, or adding new sequences to a given nucleic acid molecule.

BACKGROUND OF THE INVENTION

Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning (A Laboratory Manual)*, Cold Spring Harbor Laboratory, 1982, etc.

Another method for amplifying a nucleic acid molecule is by template directed extension. By far the most widely used of these methods is the "polymerase chain reaction" ("PCR") (Mullis, K. et al., *Cold Spring Harbor Symp. Quant. Biol.* 51: 263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference) which achieves the amplification of a specific nucleic acid sequence using two oligonucleotide primers complementary to regions of the sequence to be amplified.

The polymerase chain reaction provides a method for selectively increasing the concentration of a nucleic acid molecule having a particular sequence even when that molecule has not been previously purified and is present only in a single copy in a particular sample. The method can be used to amplify either single or double stranded DNA.

The PCR reaction is capable of exponential amplification of specific nucleic acid sequences. Reviews of the polymerase chain reaction are provided by Mullis, K. B. (*Cold Spring Harbor Symp. Quant, Biol.*, 51: 263–273 (1986)); Saiki, R. K., et al. (*Bio/Technology* 3: 1008–1012 (1985)); and Mullis, K. B., et al. (*Met. Enzymol.* 155: 335–350 (1987), which references are incorporated herein by reference).

There are many instances in gene cloning and recombinant DNA manipulation in which it is necessary to introduce a primer, probe, or linker sequence into a sample. The above-described nucleic acid amplification procedures are but a small subset of examples.

Often, after a particular reaction step has occurred, the continued presence of the introduced molecule is undesirable. Typically, it has been necessary to physically remove the introduced molecules from the sample. This may be a difficult and complex procedure. Thus, it would be desirable to be able to remove a predefined oligonucleotide from a sample without resorting to physical separation procedures.

In some situations, genetic manipulations have been impeded by the absence of convenient restriction sites, promoters, etc. in a desired orientation with respect to a gene sequence under investigation. It would be desirable to be able to generally alter the gene sequences on either side of a particular, user-defined target sequence.

The present invention provides methods suitable for accomplishing these goals.

SUMMARY OF THE INVENTION

The present invention provides a method for selectively amplifying the concentration of a nucleotide sequence present in RNA, comprising:

(a) annealing to an RNA molecule, the molecule having a 5' sequence, a sequence whose amplification is desired, and a 3' sequence, a primer molecule (I); the primer molecule (I) having a first region whose sequence is complementary to a sequence of the 3' sequence of the RNA molecule, and a second region, 5' to the first region, whose sequence is not complementary to any sequence of the 3' sequence of the RNA molecule, wherein the first region of the primer molecule (I) contains at least one deoxyuridine residue;

(b) extending the primer molecule (I) to thereby synthesize a first DNA molecule having a sequence substantially complementary to the 5' sequence, the sequence whose amplification is desired, and the 3' sequence of the RNA molecule, and additionally containing the second region of the primer;

(c) eliminating the RNA from the sample;

(d) copying the first DNA molecule using at least one primer (II) having a sequence substantially similar to the 5' sequence of the RNA molecule, to thereby produce a second DNA molecule complementary to the first DNA molecule;

(e) treating the first DNA molecule with UDG under conditions sufficient to eliminate the deoxyuridine residue contained therein.

(f) copying the second DNA molecule using at least one primer (III) having a sequence substantially similar to the second region of the primer (I), to thereby amplify the desired nucleotide sequence of the RNA.

The invention is particularly concerned with the embodiment wherein the RNA molecule is eliminated by enzymatic digestion.

The invention is further particularly concerned with the embodiments wherein the primer (A) has a sequence at or near its 3' end of either (1) $[dU]_n$, where n is greater than about 3, or (2) $[dU]_n dX$, where n is greater than about 2, and dX is either dG, dC, or dA.

The invention also provides a method for eliminating a dU-containing oligonucleotide from a reaction volume, comprising treating the reaction volume with UDG.

The invention also pertains to the embodiments of this method wherein the oligonucleotide is not covalently bound to another nucleic acid molecule and wherein the oligonucleotide is not annealed to another nucleic acid molecule.

The invention also provides the embodiment of the above method which comprises:

a) adding the dU-containing oligonucleotide to the reation volume;

b) permitting the oligonucleotide to become either covalently bound to another nucleic acid molecule or annealed to another nucleic acid molecule; and c) eliminating the oligonucleotide from the reaction volume by treatment with UDG.

The invention also provides a method for producing a desired nucleic acid molecule in which a sequence of the nucleic acid molecule 3' to a desired sequence has been selectively altered, comprising:

a) annealing to the nucleic acid molecule, at a site 3' to the desired sequence, a primer molecule (I), the primer molecule (I) having a first region whose sequence is complementary to a sequence of the nucleic acid molecule, and a second region, 5' to the first region, whose sequence is not complementary to any sequence 3' to the desired sequence of the nucleic acid molecule, wherein the second region of the primer molecule (I) contains at least one deoxyuridine residue; and b) extending the primer molecule (I) to thereby synthesize a first DNA molecule having a sequence substantially complementary to the nucleic acid molecule, and additionally containing the second region of the primer molecule (I).

The invention also provides embodiments of the above method, wherein the second region of the primer (I) has a sequence which is not complementary to any sequence 3' to the desired sequence of the nucleic acid molecule or wherein the first DNA molecule is copied, and then treated under conditions sufficient to remove the deoxyuridine of the DNA molecule or wherein both of the regions of the primer molecule (I) contain at least one deoxyuridine residue, and wherein the first DNA molecule is copied, and then treated under conditions sufficient to remove the deoxyuridine of the DNA molecule.

The invention also pertains to a kit for preparing a nucleic acid molecule containing:

a first container containing an oligonucleotide containing at least one exo-sample nucleotide (especially deoxyuridine);

a second container containing an enzyme (especially UDG) capable of degrading an oligonucleotide which contains the exo-sample nucleotide.

DESCRIPTION OF THE PREFERRED EMBODIMENTS

Figure 1:
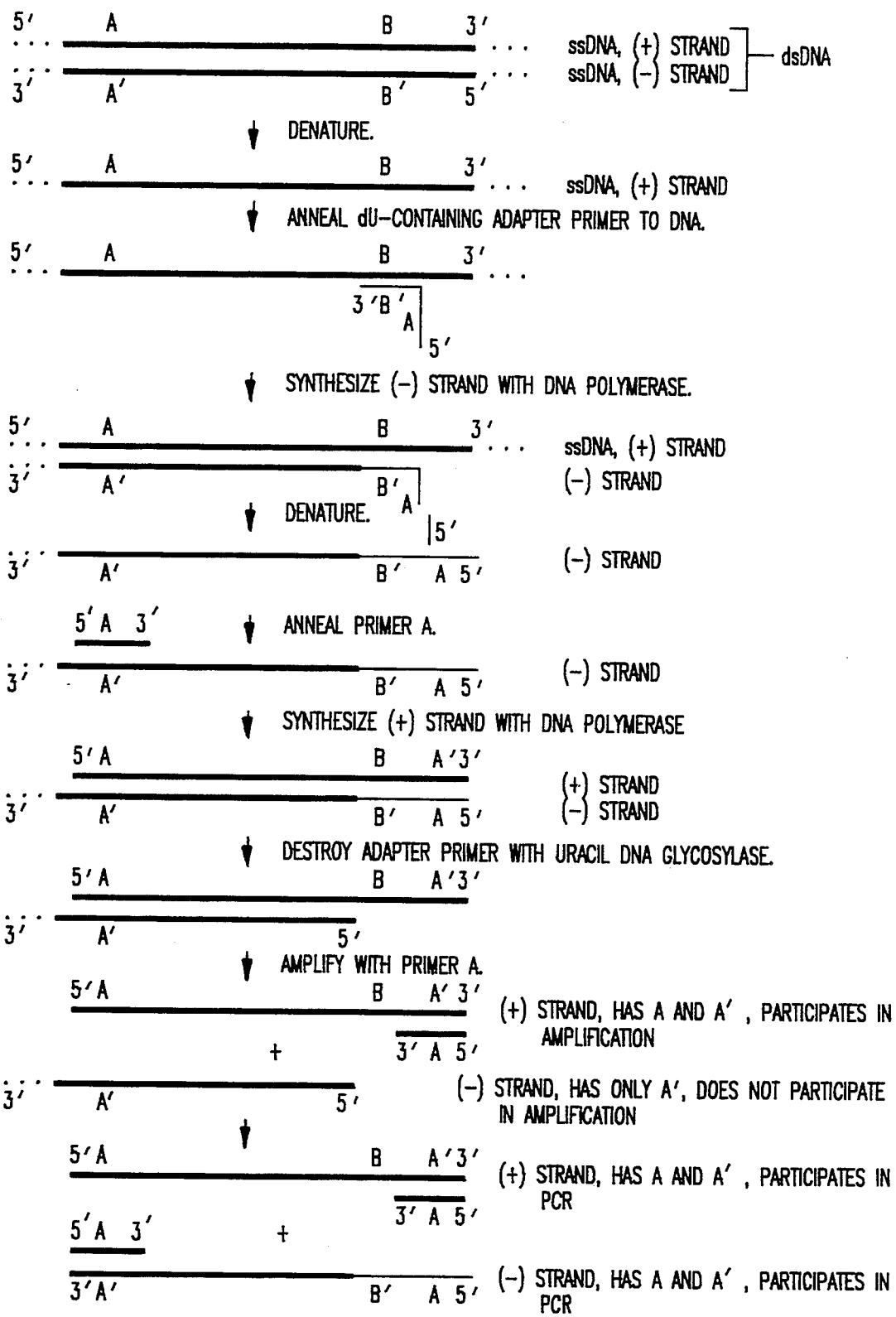
FIG. 1 shows the use of SPA to amplify a sequence with only a single primer.

The methods of the present invention allow one to selectively remove a nucleotide sequence located at either the 3' or 5' end of a user-defined target sequence. It is not necessary that either of such termini be located at the end of a nucleic acid molecule, thus, the methods of the invention can be used with circular plasmids, or to selectively remove sequences located within a linear nucleic acid molecule.

I. TERMS USED IN MOLECULAR BIOLOGY

In the description that follows, a number of terms used in molecular biology and nucleic acid amplification technology are extensively utilized. In order to provide a clearer and consistent understanding of the specification and claims, including the scope to be given such terms, the following definitions are provided.

"Amplification", as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30–100 "cycles" of denaturation and replication.

"Nucleotide" as used herein, is a term of art that refers to a base-sugar-phosphate combination. Nucleotides are the monomeric units of nucleic acid polymers, i.e. of DNA and RNA. The term includes ribonucleoside triphosphates, such as rATP, rCTP, rGTP, or rUTP, and deoxyribonucleoside triphosphates, such as dATP, dCTP, dGTP, or dTTP. A "nucleoside" is a base-sugar combination, i.e. a nucleotide lacking phosphate.

"Exo-sample nucleotide", as used herein, refers to a nucleotide which is generally not found in a sequence of DNA. For most DNA samples, deoxyuridine is an example of an exo-sample nucleotide. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g. processes involving the enzyme uracil DNA glycosylase (UDG) (Kunkel, U.S. Pat. No. 4,873,192; Duncan, B. K., *The Enzymes* XIV: 565–586 (1981), both references herein incorporated by reference in their entirety). Thus, deoxyuridine occurs rarely or never in natural DNA. It is recognized that some organisms may naturally incorporate deoxyuridine into DNA. For nucleic acid samples of those organisms, deoxyuridine would not be considered an exo-sample nucleotide. Examples of other exo-sample nucleotides include bromodeoxyuridine, 7-methylguanine, 5,6-dihyro-5,6 dihydroxydeoxythymidine, 3-methyldeoxadenosine, etc. (see, Duncan, B. K., *The Enzymes* XIV: 565–586 (1981)). Other exo-sample nucleotides will be evident to those in the art. For example, RNA primers used for DNA amplifications can be readily destroyed by base or an appropriate ribonuclease (RNase). RNase H degrades RNA of RNA:DNA hybrids and numerous single-stranded RNases are known which are useful to digest single-stranded RNA after a denaturation step.

The presence of deoxyuridine, or any other exo-sample nucleotide, may be determined readily using methods well known to the art. A nucleic acid molecule containing any such exo-sample nucleotide is functionally equivalent to DNA containing only dA, dC, dG or dT (referred to herein as T) in all respects, except that it is uniquely susceptible to certain treatments, such as glycosylase digestion. Numerous DNA glycosylases are known to the art. An exo-sample nucleotide which may be chemically or enzymatically incorporated into an oligonucleotide and a DNA glycosylase that acts on it may be used in this invention. DNA containing bromodeoxyuridine as the exo-sample nucleotide may be degraded by exposure to light under well-known conditions.

"Uracil DNA glycosylase" (UDG), a term of art, refers to an activity which cleaves the glycosidic bond between the base uracil and the sugar deoxyribose, only when the monomeric nucleotide dUTP is incorporated into a DNA molecule, resulting in incorporation of a deoxyuridine moiety (Duncan, B. in *The Enzymes* 14: 565 (1981), ed.: Boyer P). An enzyme possessing this activity does not act upon free dUTP, free deoxyuridine, or RNA (Duncan, supra).

"Incorporating" as used herein, means becoming part of a nucleic acid polymer.

"Terminating" as used herein, means causing a treatment to stop. The term includes means for both permanent and conditional stoppages. For example, if the treatment is enzymatic, a permanent stoppage would be heat denaturation; a conditional stoppage would be, for example, use of a temperature outside the enzyme's active range. Both types of termination are intended to fall within the scope of this term.

"Oligonucleotide" as used herein refers collectively and interchangeably to two terms of art, "oligonucleotide" and "polynucleotide". Note that although oligonucleotide and polynucleotide are distinct terms of art, there is no exact dividing line between them and they are used interchangeably herein. An oligonucleotide is said to be either an adapter or installation oligonucleotide (the terms are synonymous) if it is capable of installing a desired sequence onto a predetermined oligonucleotide. An oligonucleotide may serve as a primer unless it is "blocked.". An oligonucleotide is said to be "blocked," if its 3' terminus is incapable of serving as a primer.

"Oligonucleotide-dependent amplification" as used herein refers to amplification using an oligonucleotide or polynucleotide to amplify a nucleic acid sequence. An oligonucleotide-dependent amplification is any amplification that requires the presence of one or more oligonucleotides or polynucleotides that are two or more mononucleotide subunits in length and that end up as part of the newly-formed, amplified nucleic acid molecule.

"Primer" as used herein refers to a single-stranded oligonucleotide or a single-stranded polynucleotide that is extended by covalent addition of nucleotide monomers during amplification. Nucleic acid amplification often is based on nucleic acid synthesis by a nucleic acid polymerase. Many such polymerases require the presence of a primer that can be extended to initiate such nucleic acid synthesis. a primer is typically 11 bases or longer; most prefererably, a primer is 17 bases or longer. A minimum of 3 bases may, however, suffice.

"Reaction volume" denotes a liquid suitable for conducting a desired reaction (such as amplification, hybridization, cDNA synthesis, etc.).

The methods of the present invention explained below through illustration. In these illustrations, sequence pairs A and A', B and B', C and C', X and X', and Y and Y', respectively, are complementary to each other. Complementation need not be exact; homology sufficient for proper functioning, e.g. annealing and priming, will suffice.

The X sequence and the A sequence can be identical or one can be a subset of the other. In this case, amplification can be performed with a single primer. The amplification sequence X/A (X/A=X=A) is installed at the 5'-end of the DNA using the adapter primer during first strand systhesis. The second strand synthesis is also performed using the X/A amplification primer oligonucleotide for annealing to the cDNA at sequence A'. A molar excess of primer X/A over the adapter primer should improve second strand yield.

The B sequence can be the poly(A) tail of an mRNA. In this case, B' is oligo(dU). If one wishes to ensure that the adapter primer oligonucleotide sits down on the poly(A) tail at the 5'-end of the tail, the 3'-end of the adapter primer should not be dU or dT. In other words, the 3' end of B' preferably ends with dA, dG or dC. The sequences need not be homopolymers of dU, but may contain both dU and T.

II. ELIMINATION OF NON-COVALENTLY BOUND NUCLEIC ACID MOLECULES

The methods of the present invention can be used to eliminate a nucleotide sequence which may be present in a sample.

If the molecule containing the eliminated sequence is not covalently bound to other molecules of the sample (for example, a probe, a non-extended primer or an-unligated linker sequence), the method of the invention serves to eliminate such nucleic acid molecules from the sample.

Alternatively, if the eliminated sequence had been covalently linked to other sequences of the sample, then the methods of the invention result in the production of a gap at the site of the eliminated sequence. As disclosed in detail below, this gap can, if desired, be "filled in" so as to introduce a user-defined desired nucleotide sequence into the "gap" region. The user-defined desired sequence may comprise a restriction site, promoter region, replication origin, recombinase recognition sites, such as loxP (Hoess, R., et al., *Proc. Natl. Acad. Sci. (U.S.A.)* 79: 3398–3402 (1982); Sauer, B. L., U.S. Pat. No. 4,959,317, herein incorporated by reference), λatt (Weisberg, R. et al., In: Lambda II, (Hendrix, R. et al., Eds.), Cold Spring Harbor Press, Cold Spring Harbor, N.Y., pp. 211–250 (1983), herein incorporated by reference), etc. Significantly, the user-defined desired sequence may be of any length, and may encompass one or more structural genes.

The use of ligated promoter regions is disclosed by Berninger et al. in U.S. patent application Ser. No. 07/524,306 (filed May 16, 1990), herein incorporated by reference. This reference discloses a method which requires a defined 5'-end on a target RNA sequence or a defined 3' end on a DNA target sequence. In contrast, the present invention permits one to incorporate a promoter region into a DNA molecule which does not have a defined 5'-end.

Thus, in one embodiment, the methods of the present invention may be used to remove one or more predefined oligonucleotides which may be present in a sample. Such nucleotide sequences will, typically, have been deliberately introduced into a sample for a desired purpose (such as to serve as a primer of nucleic acid replication, a hybridization probe, a linker sequence, etc.). After the purpose has been fulfilled, the continued presence of the oligonucleotide may be undesirable. In general, it has been necessary to remove the introduced oligonucleotide using physical means (centrifugation, electrophoresis, etc.). Since, the oligonucleotide is similar in composition and structure to other oligonucleotides of the sample (whose removal is not desired), such physical means are generally inefficient and/or time consuming.

The present invention accomplishes this goal by employing, as the introduced nucleic acid molecules of defined sequence, molecules which contain one or more exo-sample nucleotides. Such nucleotides may be, and preferably will, be of the same type (i.e. all dU); alternatively, several differnt types of exo-sample nucleotides may be employed in the molecule. The removal of the introduced molecule is accomplished by treating the sample with an enzyme capable of hydrolyzing nucleic acid molecules which contain the exo-sample nucleotide (for example, by incubating the sample in the presence of UDG to remove all dU-containing sequences). This method is applicable to any in vitro procedures which utilize enzymes to amplify specific nucleic acid sequences and especially to PCR.

The use of one embodiment of this method to remove potential contaminants from samples being subjected to PCR amplification is disclosed by Berninger in U.S. patent application Ser. No. 07/401,840 (filed Sep. 1, 1989), by Hartley, J. L., U.S. patent application Ser. No. 07/360,120 (filed Jun. 1, 1989), and by Longo, M. C. et al. (*Gene* 93: 125–128 (1990)), all of which references are herein incorporated by reference in their entirety. These references disclose the use of either dU-containing oligonucleotides or dUTP in the PCR-directed amplification of a target sequence. The sample is treated with UDG prior to amplification in order to eliminate any dU-containing DNA (derived from other prior PCR reactions) which may have contaminated the sample. The methods thus eliminate contamination of starting materials with the end products of previous amplification processes, and thereby address a major problem of nucleic acid amplification techniques.

Another aspect of the invention is illustrated in FIG. 1 with respect to single-primer amplification (SPA) of a DNA molecule (as represented below, " " denotes dT-containing ssDNA; " " denotes dU-containing ssDNA; and " . . . " denotes continuing sequences). The use of SPA permits one to amplify a sequence without employing PCR (which requires two primers) as shown in FIG. 1.

Incorporation of an exo-sample nucleotide into a primer allows the DNA or RNA produced during such amplification processes to be differentiated from the original nucleic acids present in the sample prior to amplification. If desired, the amplification reaction itself may, in addition, further provide exo-sample nucleotides for incorporation into the replicating nucleic acid, for example, as taught by Hartley, supra.

Typically, primers are used wherein one or more of the four ribonucleotides (ATP, UTP, CTP and GTP), or deoxyribonucleotides (dATP, dTTP, dCTP and dGTP), in the oligonucleotide are replaced with one or more exo-sample nucleotides. Embodiments utilizing primers with high proportions of exo-sample nucleotides are preferred over those with fewer exo-sample nucleotide-containing oligonucleotides. Primers with a high fraction of exo-sample nucleotides located at the 3'OH region of the primer are preferred. In another preferred embodiment, an exo-sample nucleotide is the 3' nucleotide.

Primer A need not be used in the PCR amplification. One can use another primer, 3'-to Primer A, i.e. complementary to the first strand between sequences A and B. Nested primers are appropriate in a re-amplification reaction.

Synthesis of DNA is performed using a DNA polymerase. When RNA is employed, first strand synthesis is performed with an RNA-dependent DNA polymerase. In a preferred embodiment, an RNase H$^-$ polymerase such as SUPERSCRIPT ™ (BRL) is employed.

Second strand synthesis is done with the residual reverse transcriptase remaining form first strand synthesis. Reverse transcriptase will use either ssDNA or ssRNA as a template. Alternatively, one can add a new DNA polymerase for second strand synthesis.

The installation oligonucleotide may also have dT, if the dU, both quantitatively and in location, is sufficient to cause the UDG-treated oligonucleotide to not function as a primer.

In a preferred embodiment, the deoxyribonucleotide deoxyuridine is used as an exo-sample nucleotide which may be conveniently incorporated into primers used in an oligonucleotide-dependent DNA amplification procedure, exemplified herein by PCR, thereby resulting in deoxyuridine-containing, DNA amplification products.

Discrimination between a nucleic acid which does not contain the exo-nucleotide deoxyuridine and a deoxyuridine-containing product of an amplification reaction may be obtained with the enzyme UDG. Treatment of DNA containing uracil bases with UDG results in cleavage of the glycosidic bond between the deoxyribose of the DNA sugar-phosphate backbone and the uracil base. The loss of the uracil creates an apyrimidinic site in the DNA, which blocks DNA polymerase from using the DNA strand as a template for the synthesis of a complementary DNA strand (Schaaper, R. et al. *Proc. Natl. Acad. Sci. USA* 80: 487 (1983).

By providing primers containing exo-sample nucleotides, such exo-sample nucleotides are localized at the 5' ends of each strand of DNA template which is amplified. When deoxyuridine-containing primers have been used and the sample treated with UDG, substantial numbers of apyrimidinic sites in the 5'-end of each DNA target template molecule are found. Such apyrimidinic sites interfere with synthesis of sequences at the 3'-end of newly made strands. These 3'-end sequences are the targets to which original exo-sample-containing primers bind. Thus these primers do have target sequences with which they can bind an nucleic acid derived from molecules primed by exo-sample nucleotide-containing primers.

Embodiments having a greater proportion of oligonucleotides containing exo-sample nucleotides are preferred. However, even in standard PCR embodiments that depend on two oligonucleotide primers, the present invention is capable of rendering PCR contaminants unamplifiable as long as at least one primer contains an exo-sample nucleotide.

Not all single exo-sample nucleotide-containing primers may be eliminated to a desired extent by treatment with a glycosylase, light, or other eliminating agent. Those of ordinary skill in the art can empirically find which primers are acceptable during routine optimization without undue experimentation.

Routine assay optimization, aimed at testing oligonucleotide suitability, can be done by (1) making an exo-sample nucleotide-containing oligonucleotide, (2) adding that oligonucleotide to a sample, (3) treating the sample to eliminate the oligonucleotide, and (4) determining whether such treatment has achieved a desired degree of elimination.

III. SELECTIVE AMPLIFICATION FROM AN RNA TARGET

One embodiment of the above-describe method permits one to amplify a target from RNA, which may be polyadenylated (e.g. messenger RNA (mRNA)) or not polyadenylated, in the presence of denatured or native DNA of identical or substantially similar sequence and/or size. The method thus permits preferential amplification of RNA over DNA.

The method utilizes the endonuclease activity of ribonuclease H (RNase H) which is specific for RNA:DNA heteroduplex, in order to differentiate between RNA and DNA. The use of a DNA glycosylase (such as UDG) is then critical for the destruction of the original adapter oligonucleotide (to prevent its participation in subsequent amplification using DNA as target).

In a preferrred method, first-strand synthesis is performed using an RNA-dependent DNA polymerase activity. First-strand synthesis is initiated from a primer (e.g. an adapter primer (AP)) which contains a sequence which is dU-containing and which would not ordinarily be present in a particular RNA substrate of interest. More efficient synthesis may be accomplished if the reverse transcriptase activity is lacking an RNase H component.

The RNA template is denatured or destroyed in a way which does not separate DNA duplex strands (e.g. RNase H or an RNA:DNA -specific helicase). Any means capable of rendering the cDNA sufficiently single-stranded to permit primer annealing for second strand synthesis may alternatively be used. Once rendered single-stranded, the cDNA product of first strand synthesis is primed using an oligonucleotide and an appropriate polymerase (e.g. reverse transcriptase or an appreoriate DNA polymerase, such as taq polymerase).

Critical to this preferred embodiment of the invention is the substantial, selective destruction of the dU-containing sequences (e.g. installation primer incorporated into the first strand of cDNA, or excess installation primer present in the reaction volume). One method for accomplishing this goal utilizes uracil DNA Glycosylase (UDG) which enzymatically converts dUMP sites with the adapter primer region to abasic sites. Subsequent heating converts these sites to strand breaks such that the adapter primer is no longer suitable for priming.

Figure 2:
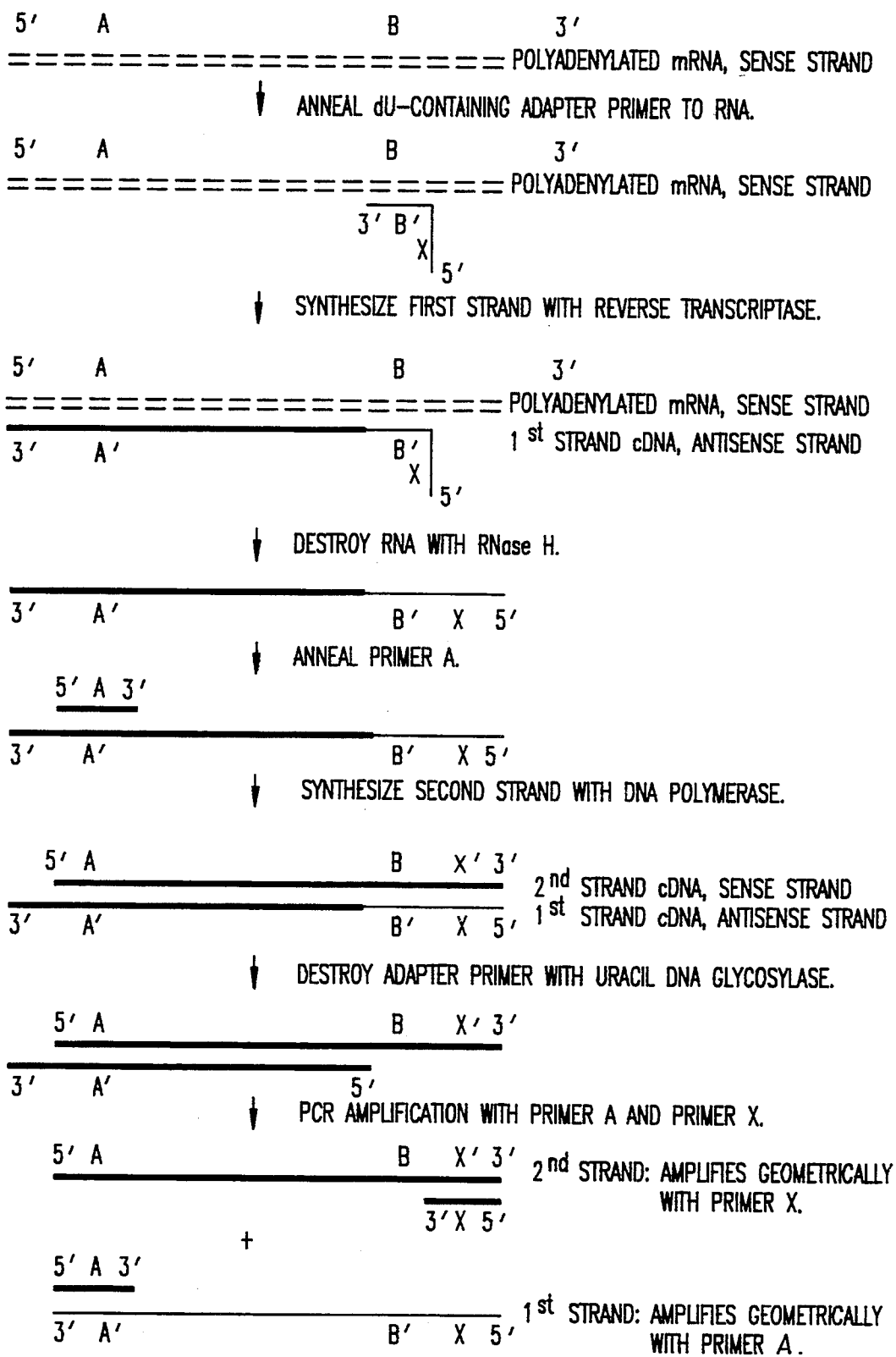
FIG. 2 illustrates a method of amplification that employs dU-containing DNA. In the figure, "——" denotes dT-containing single stranded DNA; "==" denotes ssRNA; "—" denotes dU-containing single stranded DNA.

This method is illustrated in FIG. 2 with respect to polyadenylated mRNA; it is applicapble, however, to any RNA species. In the depiction, "—" denotes dT-containing single stranded DNA as shown in FIG. 2; "—" denotes ssRNA; "==" denotes dU-containing single stranded DNA.

It is to be noted that since single- or double-stranded DNA is not degraded by RNAse H, a newly synthesized template formed from a DNA (rather than an RNA) template will not be accessible for subsequent amplification. Thus, only sequences present in DNA will be amplified. An identical sequence found in the DNA of a sample will not be amplified. This method has substantial value in cDNA synthesis, and in RNA virology and diagnostics, on the study of gene expression, and in other circumstances where one desires to selectively amplify RNA species.

In one embodiment of this method, one can selectively amplify a sequence found in the RNA, as opposed to the DNA, contained in a sample.

To achieve this goal, one anneals an RNA sequence which is to be amplified (this sequence may be a subset of the sequences present on an RNA molecule) to a first DNA oligonucleotide (complementary to the RNA sequence which is to be amplified) and containing an exo-sample nucleotide (preferably dU). The oligonucleotide has a free 3' hydroxyl terminus, and can therefore serve as a primer for template-directed DNA synthesis.

The annealed molecule is incubated in the presence of all compounds, enzymes and co-factors needed to permit the synthesis of a first strand cDNA by a reverse transcriptase (RNA-dependent DNA polymerase). The first oligonucleotide serves as a primer in this reaction and the RNA molecule as a template, whereby the first oligonucleotide forms the 5'-end off the first strand cDNA.

Once synthesis has been completed, the RNA template is removed from the synthesized first strand cDNA (preferably enzymatically).

A second DNA oligonucleotide is then permitted to anneal to the first strand cDNA at a location on the first strand cDNA 3' to (not opposite to) the location bound by the first oligonucleotide. This second oligonucleotide is used to synthesize a second strand cDNA with a DNA polymerase (which may or may not be reverse transcriptase) using the DNA primer as a primer and the first strand cDNA molecule as a template, whereby the DNA primer forms the 5'-end of the second strand cDNA.

If the second oligonucleotide (rather than the first) contains the exo-sample nucleotide (preferably dU), one creates a free 3'-overhang of the cDNA complementary to the dU-containing sequence.

A sequence encoded in either or both of the first strand or the second strand can then be amplified using a third oligonucleotide that anneals to the 3'-overhang produced above.

In an alternative method for achieving the selective amplification of a sequence present on an RNA molecule, one anneals the RNA sequence to be amplified to a DNA adapter primer oligonucleotide, which contains deoxyuracil and has a 3'-end which is substantially complementary to the 3'-end of the RNA sequence to be amplified.

One then synthesizes a first strand of cDNA with reverse transcriptase using the adapter primer as a primer and the RNA molecule as a template, whereby the adapter primer forms the 5'-end of the first strand cDNA.

For the selective amplification of RNA-containing sequences, RNA is eliminated by an RNAse activity, or by a DNA:RNA -helicase. For other amplification protocols (such as RACE, anchored PCR, one-sided PCR, etc.), elimination can also be accomplished by physical denaturation, e.g. heat, formamide, or alkali (high pH), etc.

A second strand of cDNA is synthesized with a DNA polymerase (which may or may not be reverse transcriptase) using the DNA primer as a primer and the first strand cDNA molecule as a template, whereby the DNA primer forms the 5'-end of the second strand cDNA.

The adapter primer is degraded with uracil DNA glycosylase, thereby forming a free 3'-overhang of the second strand cDNA. The desired molecule may then be amplified, as with PCR, etc. using a first primer having a sequence substantially complementary to a complement of the adapter primer and a second primer whose sequence is substantially complementary to a complement of the RNA at or 3' to the 5' end of the second strand cDNA.

IV. ELIMINATION OF COVALENTLY BOUND NUCLEIC ACID MOLECULES

In this embodiment of the invention, a nucleic acid molecule containing a sequence which contains an exo-sample nucleotide is treated so as to eliminate the sequence and produce a gap in the nucleic acid molecule. Most preferably, the exo-sample nucleotide will be dUTP. The exo-sample nucleotide-containing sequence may be introduced into the nucleic acid molecule in any of a variety of ways. It may be incorporated into the a molecule through DNA synthesis in the presence of the exo-sample nucleotide. Alternatively, it may be added, through ligation, to a terminus of a nucleic acid molecule. Most preferably, however, it is introduced into the molecule by extending an exo-sample nucleotide-containing primer.

In a preferred embodiment, a dU-containing primer is used to prime synthesis of dT-containing DNA. The primer is then eliminated from the extension product by UDG treatment. Then, another oligonucleotide can be annealed to the template or similar molecule in the location that would otherwise be occupied by the primer.

In a narrower form of the invention, a dU-primer is extended with dT to form a first strand, the first strand is copied with dT to form a second strand that is complementary to the extension product and the primer, the primer is removed by UDG, and then another oligonucleotide is annealed to the second strand in the position formerly occupied by the primer.

A. USE IN "RACE" AND SIMILAR PROCEDURES

The invention may thus be used in the 3' and 5'RACE procedures (Frohman, M. A. et al., *Proc. Natl. Acad. Sci. (U.S.A.)* 85: 8998–9002 (1988); Ohara, O. et al., *Proc. Natl. Acad. Sci. (U.S.A.)* 86: 5673–5677 (1989), both of which references are herein incorporated by reference). These procedures are also known as "one-sided PCR" or "anchored-PCR." In brief, these procedures facilitate the recovery of full-length cDNAs from rare transcripts. The RACE procedure results in the amplification (using PCR, for example) of sequences 3' and 5' of a particular sequence known to be present in a desired molecule.

Figure 3:
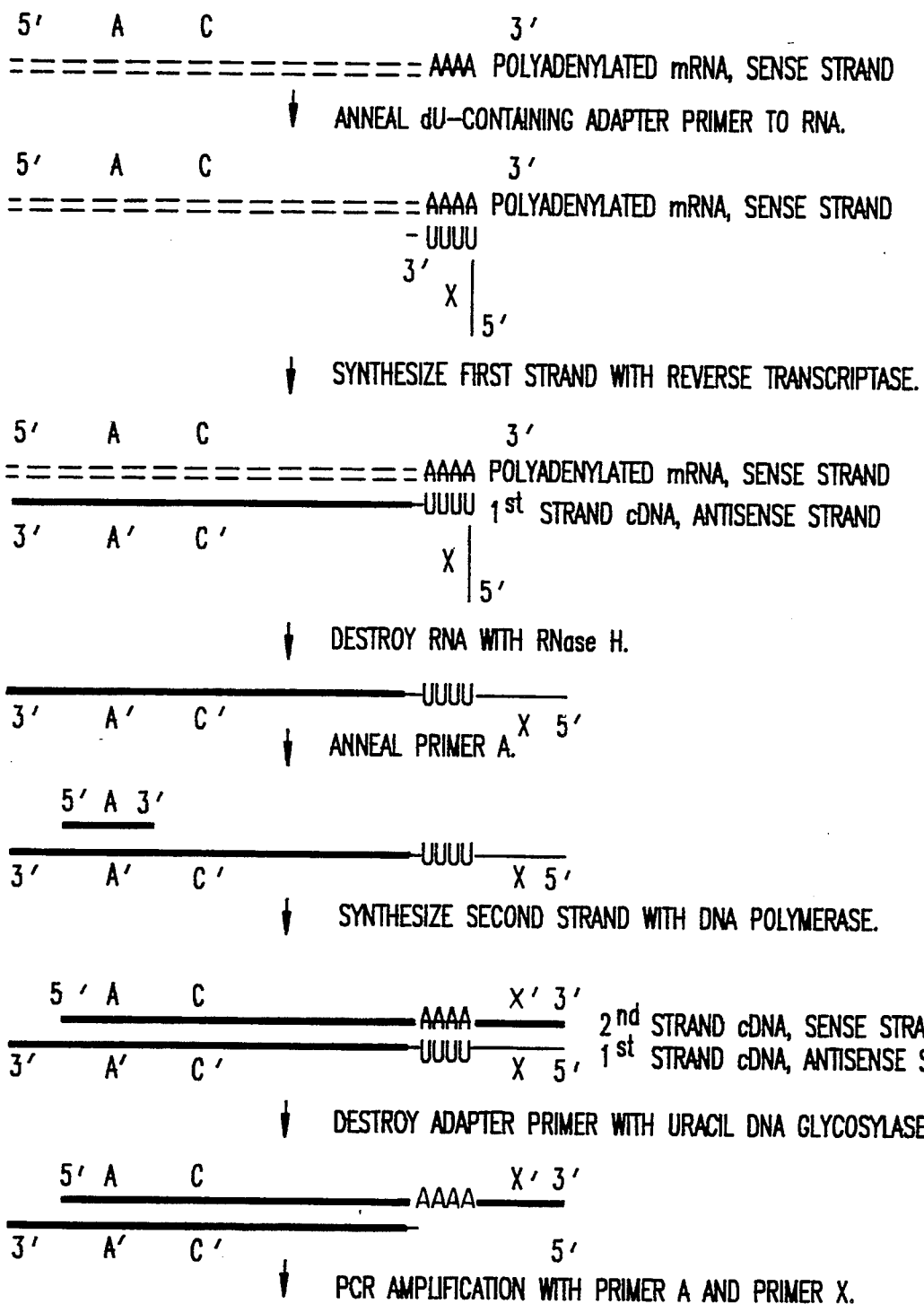
FIG. 3 illustrates a 3' RACE aspect of the invention. In the figure, "——" denotes dT-containing single stranded DNA. "==" denotes ssRNA; "—" denotes dU-containing single stranded DNA.
Figure 3:
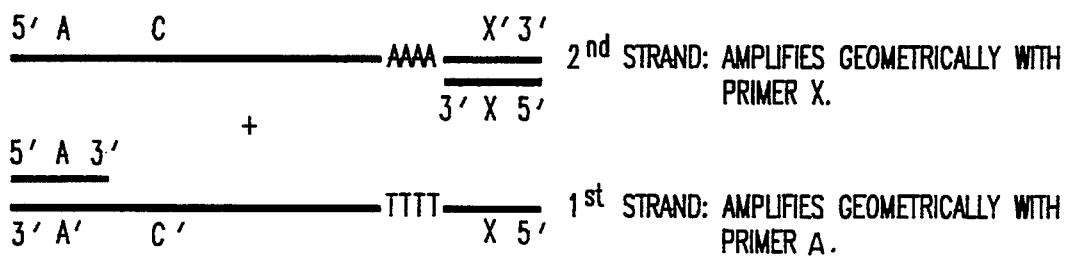
Figure 3:
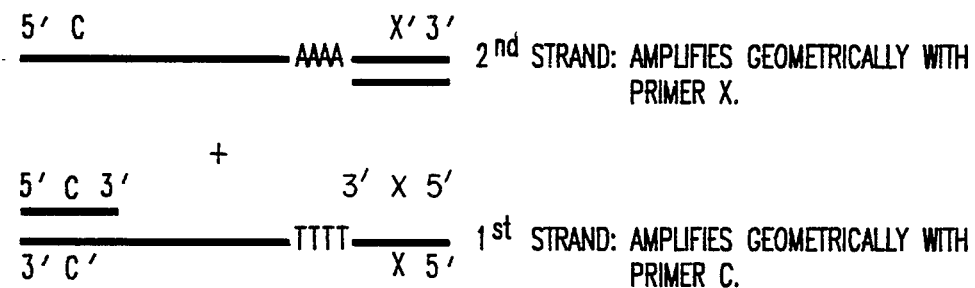

The 3' RACE aspect of the invention is illustrated in FIG. 3, where "—" denotes dT-containing single stranded DNA as shown in FIG. 3; "≈≈" denotes ssRNA; "—" denotes dU-containing single stranded DNA.

Figure 4:
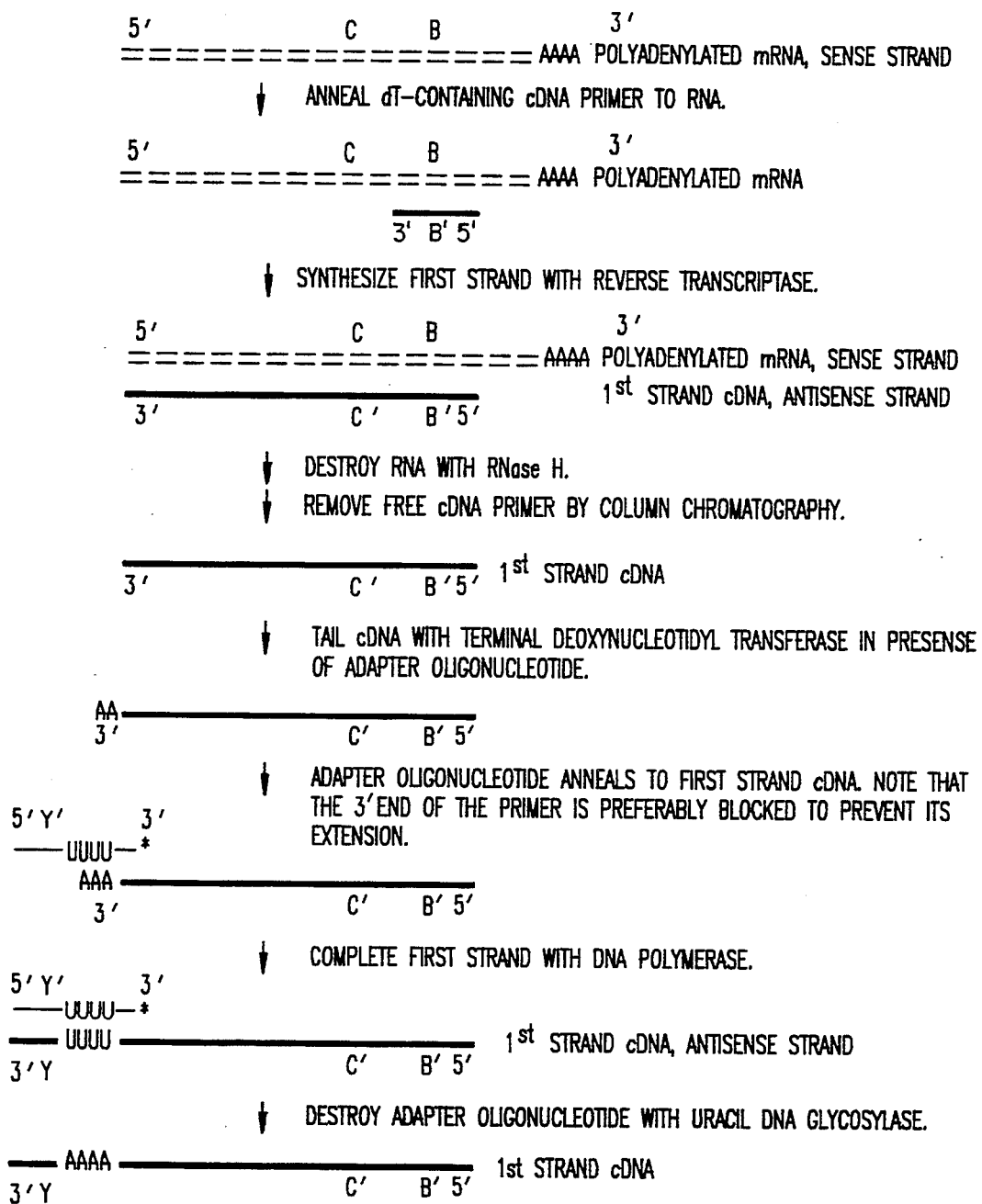
FIG. 4 illustrates a 5' RACE aspect of the invention. In the figure, "——" denotes dT-containing single stranded DNA; "==" denotes ssRNA; "—" denotes dU-containing single stranded DNA; and "*" denotes that the 3' end is blocked.
Figure 4:
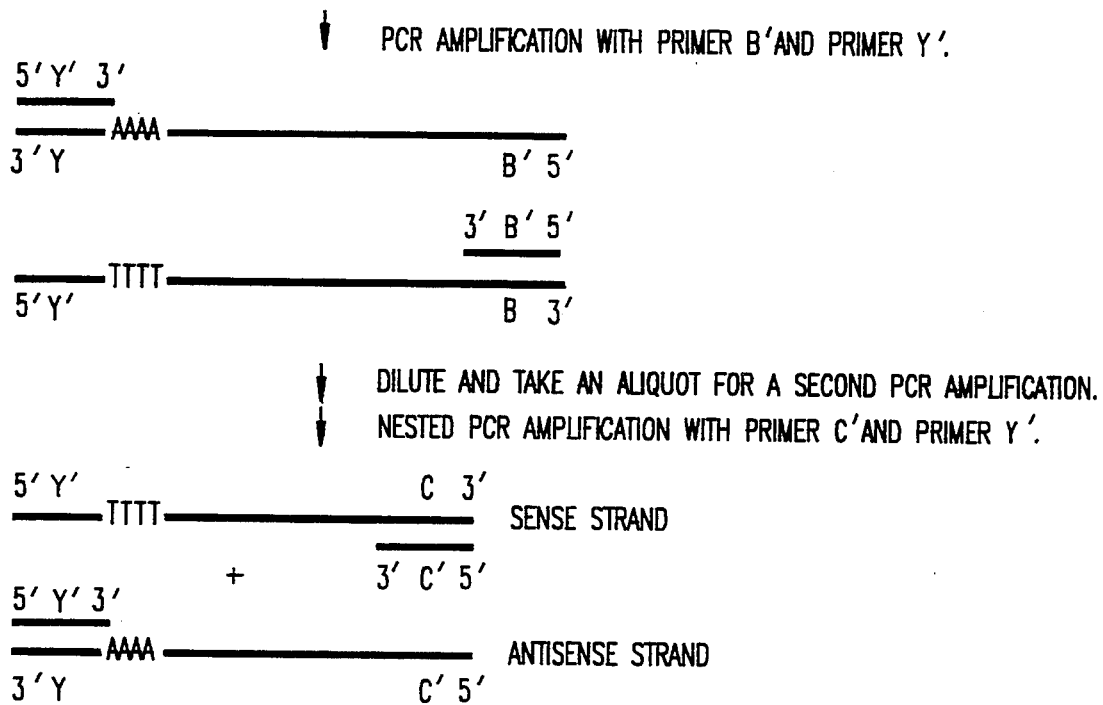

The 5' RACE aspect of the invention is illustrated in FIG. 4, where "—" denotes dT-containing single stranded DNA; "≈≈" denotes ssRNA; "—" denotes dU-containing single stranded DNA; and "*" denotes that the 3' end is blocked.

The results of both the 3' and 5' RACE procedures can be combined to enable the amplification of the entire nucleic acid molecule.

A problem with conventional methodologies is that poly(A):poly(dT) has a low $T_m$, therefore a low specificity of annealing. Thus, high levels of the adapter primer in the 3'-RACE improves first strand synthesis. Elimination of the adapter primer by UDG prevents non-specific artifacts which may occur during subsequent amplification. Removal of the primer prevents subsequent priming.

It should be noted that both the 3' and 5'-RACE procedure may generate artifact products unless nested PCR is done. Nested PCR (which is a preferred method of amplification) is disclosed in U.S. Pat. Nos. 4,683,195 and 4,683,202. Nested PCR may also be used for the products of 3'-RACE to eliminate non-specific amplification products. Note that nested PCR often refers to PCR with primers "nested" at both ends of the sequence, i.e. PCR conducted using 4 oligonucleotides. Here, it is nested only at one end; only 3 PCR oligonucleotides need be used.

Also of significance is the fact that in the illustrated RACE schemes, the 3'-end of the dU-containing adapter primer oligonucleotide is shown as being dU-containing. Preferably, however, it is either dA, dG, or dC, but not either dU or dT. (preferably, a degenerate mixture of dA, dG, and dC is used.) This forces the adapter primer to prime synthesis of the first strand starting at the 5'-end of the poly(A) tail. By its nature, this part of the sequence cannot be said to be either dU-containing or dT-containing. It is depicted as being dU-containing to clarify its origin in subsequent steps. The reactions in the RACE schemes can be designed to use an adapter primer without this "extra" non-dU nucleotide at the 3'-end.

An advantage of the use of the methods of the present invention in RACE procedures goes beyond elimination of amplification products derived from contaminating DNA. One problem with prior art RACE schemes that used equimolar (relatively low) amounts of adapter primer and mRNA is that the excess adapter primer led to PCR artifacts, assumed to be due to non-specific priming. The present invention allows one to use excess adapter primer, thereby increasing the amount of the desired cDNA produced without the production of such artifacts.

Moreover, in the methods of the prior art one diluted the oligo(dT):mRNA complex before reverse transcription in order to minimize non-specific PCR products. This dilution results in fewer RACE products to be PCR amplified. The present invention, by avoiding the dilution step, increases the chances of finding the products of already rare mRNAs.

The present invention also provides a method for controlling the length of tailing by terminal deoxynucleotidyl transferase (TdT). This method is useful as part of 5'-RACE reaction.

When a tailing reaction is performed in the presence of a complementary homopolymer oligonucleotide (preferably, oligo(dU)), poly(dA) tails are limited in length to about 17 nucleotides in length. In the absence of the homopolymer, tails can extend hundreds of bases (e.g. greater than 400 bases has been observed). The 3'-end of the adapter oligonucleotide must be blocked so that it cannot serve as a primer; otherwise it will become poly(dA) tailed and various artifacts will be produced. Therefore, one must remove the adapter oligonucleotide (as by UDG treatment) and use a separate, dT-containing adapter primer in subsequent PCR steps.

Figure 5:
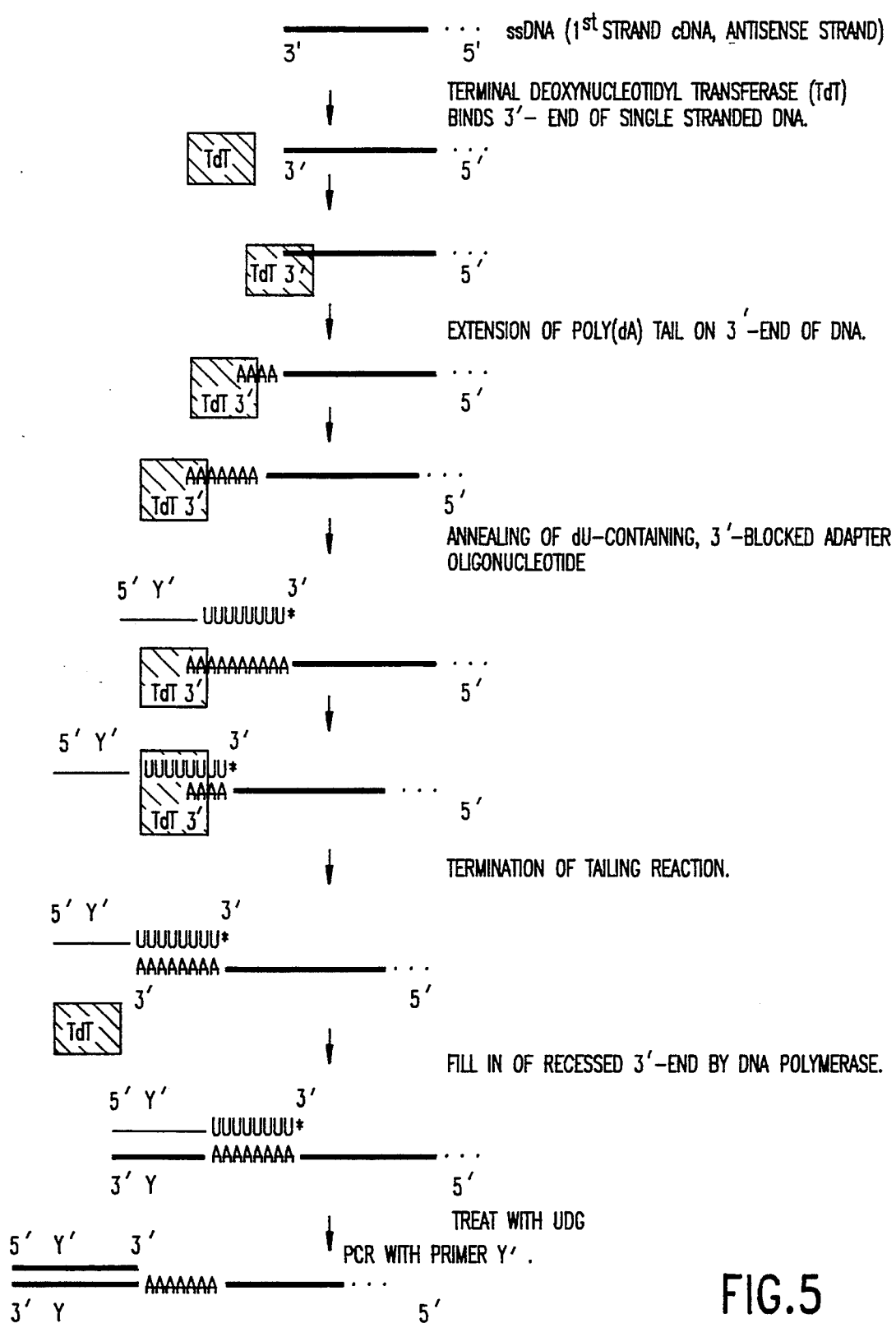
FIG. 5 illustrates a method of amplification which controls the length of tailing by terminal deoxynucleotidyl transferase (TdT). In the figure, "——" denotes dT-containing ssDNA; "—" denotes dU-containing ssDNA; "*" denotes a blocked 3'-nucleotide, "▒" denotes an enzyme, and " . . . " denotes continuing sequences.

The method which controls the length of tailing by terminal deoxynucleotidyl transferase (TdT) is explained by way of illustration in FIG. 5 (in the depiction, "—" denotes dT-containing ssDNA; "—" denotes dU-containing ssDNA; "*" denotes a blocked 3'-nucleotide, "▩" denotes an enzyme, and " . . . " denotes continuing sequences as shown in FIG. 5.

2. USE IN LIGATION ACTIVATED TRANSCRIPTION PROCEDURES

As illustrated below, the present invention also permits one to install (attach) a short, defined sequence at the 5'-end of a cDNA molecule. The method utilizes an oligonucleotide primer (adapter primer, AP) molecules containing:

a) a sequence (B') which is user-defined and complementary to a nucleic acid analyte sequence of interest (B) (which may be RNA; if RNA analytes are used, then after adapter primer extension, the RNA template strand should be separated or destroyed; and b) a defined sequence (X) which is identical to proto-promoter region (X).

The adapter primer may contain only sequence B' proto-promoter would then have the B' sequence at its 3'-blocked single-stranded end.

The oligonucleotide primer XB' is annealed to the single-stranded nucleic acid analyte, and extended using an appropriate polymerase. The resultant primer extension product is heat-denatured and then rendered duplex from primer A using polymerase. Uracil DNA glycosylase (UDG) is used to destroy residual, unextended adapter primer and to form a single-stranded region on the duplex analyte which may anneal to proto-promoter. Destruction of residual adapter primer is critical to avoid its competition with proto-promoter annealing to the X sequence (i.e., thermal denaturation to render the X analyte sequence would be a substrate for annealing to both adapter primer and proto-promoter molecules).

After annealing to a proto-promoter, Ligation Activated Transcription (LAT) proceeds. LAT is described in U.S. patent application Ser. No. 07/542,306 (filed May 16, 1990), now U.S. Pat. No. 5,194,370, herein incorporated by reference in its entirety). Two embodiments of this aspect of the invention are illustrated below, where "—" denotes dT-containing single stranded DNA; "..." denotes continuing sequences; "—" denotes dU-containing single stranded DNA, and "*" indicates a blocked 3' terminus.

Figure 6:
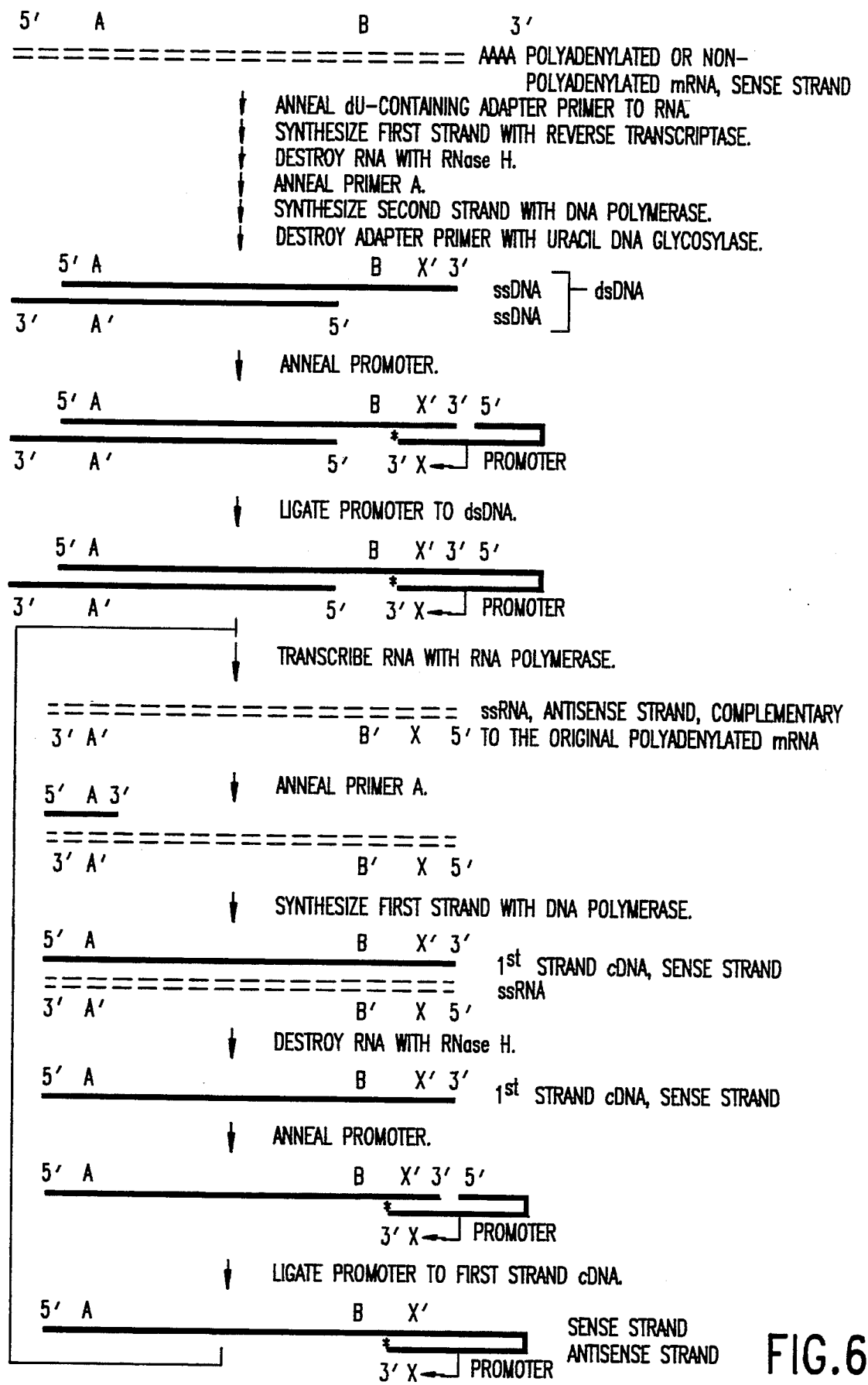
FIG. 6 illustrates an adaptation of a method of the invention to work with an isothermal amplification scheme that cycles between RNA and DNA by alternating between transcription and reverse transcription.

The first embodiment shows how the methods of the present invention can be adapted to work with an isothermal amplification scheme that cycles between RNA and DNA by alternating between transcription and reverse tanscription (such a scheme, is described in U.S. patent application Ser. No. 07/524,306). The RNA polymerase is preferably from phage T7. The 3'-end of the promoter oligonucleotide is blocked so that it cannot serve as a primer for DNA synthesis. Transcription is dependent on ligation of the promoter oligonucleotide to the template. In the illustration, the promoter oligonucleotide is depicted as a single chain hairpin; it may also be configured as two chains non-covalently based-paired together. The target nucleic acid can be either RNA or DNA. The target must have a defined 5'-end on an RNA target sequence, or a defined 3' end on a DNA target sequence as shown in FIG. 6.

Figure 7:
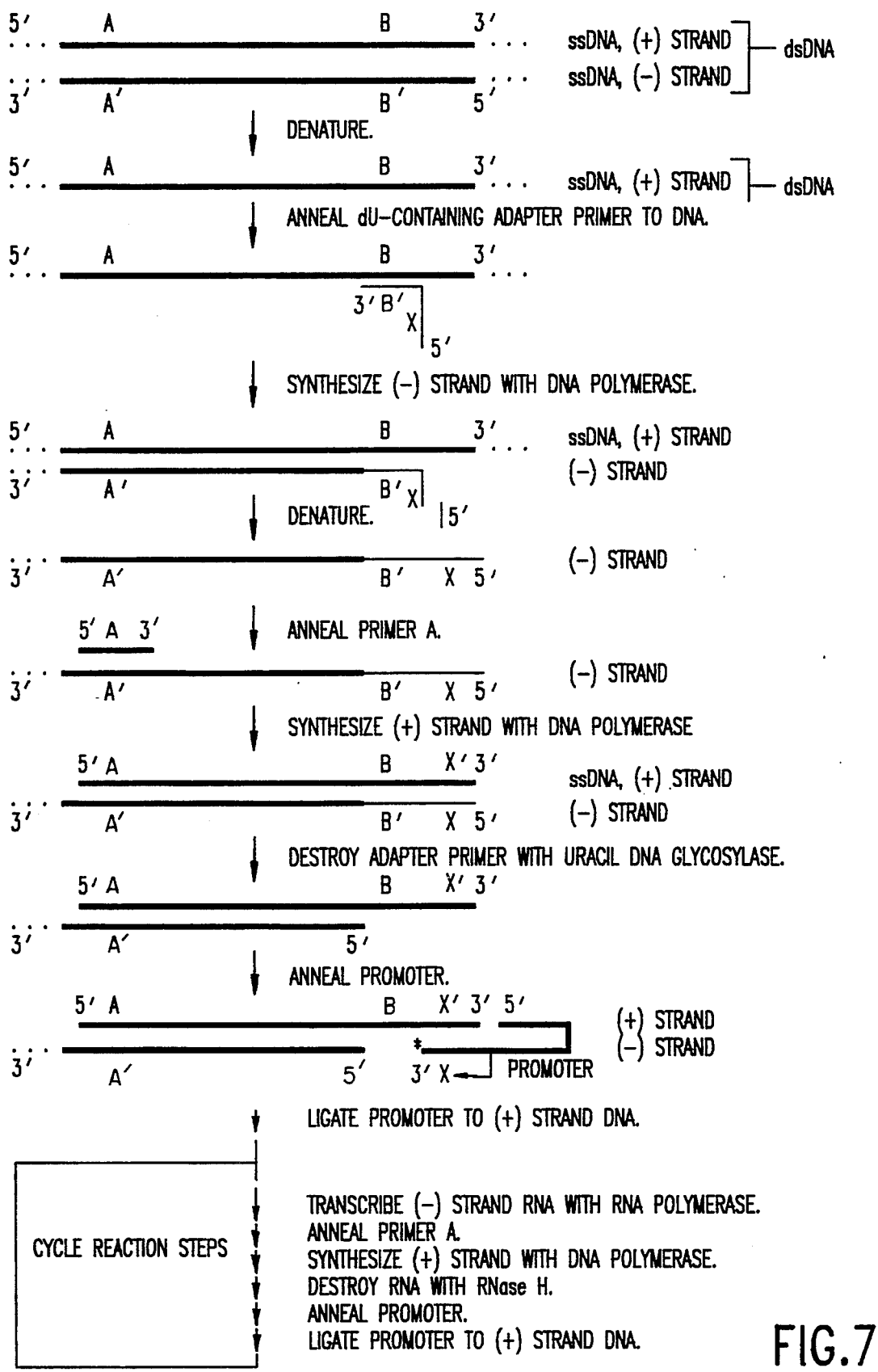
FIG. 7 shows how to adapt the method shown in FIG. 6 to amplify a nucleic acid, (DNA in the figure), that does not have a defined 3'-end.

The second embodiment of this aspect of the invention, shows how to adapt the above scheme to amplify a nucleic acid, here DNA, that does not have a defined 3'-end (FIG. 7).

It is to be noted that the above method creates a desired terminus without the necessity for a restriction enzyme.

The present invention includes articles of manufacture, such as "kits." Such kits will, typically, be specially adapted to contain in close compartmentalization a first container which contains an exo-sample nucleotide or an exo-sample nucleotide-containing oligonucleotide (such as dUTP or dU); a second container which contains an enzyme capable of degrading an oligonucleotide which contains the exo-sample nucleotide. The kit may additionally contain buffers, RNAse enzymes, instructional brochures, and the like.

Having now generally described the invention, the same will be more readily understood through reference to the following examples which are provided by way of illustration, and are not intended to be limiting of the present invention, unless specified.

EXAMPLE 1

AMPLIFICATION OF A NUCLEIC ACID SEQUENCE OF AN RNA MOLECULE

Materials and Methods

Reagents: All buffer components and enzymes were from BRL. Deoxynucleotide triphosphates (dNTPs) were from Pharmacia, and actinomycin D (AcD) from Boehringer Mannheim. All dU-containing oligonucleotide primers were prepared using stranded phoramidite chemistry. Oligonucleotide primer sequences were as follows:

Oligo 1: (SEQ ID NO: 1)
5' GGGAGACCGG AAUUCUCCUU CAAUUGCUGA UGCAGGUGAC 3'

Oligo 2: (SEQ ID NO: 2)
5' CTGCATGATA ATATATGTTT GTGCG 3'

Oligo 3: (SEQ ID NO: 3)
5' GGGAGACCGG AATTCTCC 3'

Oligo 1 is an installation oligonucleotide. Oligo 2 is the primer for second strand synthesis and PCR. Oligo 3 is the second PCR primer.

Preparation of RNA Analyte: A DNA segment from the L1 region of Human Papilloma Virus (HPV) type 16 was cloned into plasmid vector pT7-13 (BRL) behind a T7 RNA Polymerase promoter. In vitro transcription was performed using T7 RNA polymerase (BRL, 12,000 U) and 10 μg of plasmid template in the presence of inorganic pyrophosphatase (ICN, 25 U) and Human Placental RNase Inhibitor (Promega, 200 U) in a 1 ml reaction. The reaction was incubated for 60 min at 37° C., then extracted once with phenol:chloroform (1:1 v:v). The DNA template was degraded using deoxyribonuclease (DNase) free of ribonuclease (RNase) (BRL). The RNA transcript was purified by G-50 (Pharmacia) size exclusion column chromatography. Equilibration and elution buffer was TE (TE: 10 mM Tris.HCl (pH 7.5), 1 mM Na$_2$EDTA; EDTA: ethylene diaminetetraacetic acid) containing 100 mM NaCl and 0.1% SDS.

cDNA Synthesis: First strand cDNA synthesis was performed using oligo 1 (500 nM or 100 nM) as a primer. The reaction, assembled on ice, contained 500 $\mu$M each of the four dNTPs, 10 mM dithiothreitol (DTT), 1.0 $\mu$g/ml AcD, 200 U SUPERSCRIPT ™ reverse transcriptase (MMLV-RT RNase H$^{-1}$: BRL), 20 mM Tris.HCl (pH 8.4), 50 mM KCl, 2.5 mM MgCl$_2$, and 100 $\mu$g/ml bovine serum albumin (BSA: BRL). The reaction was incubated at 42° C. for 20 min. RNA template was then removed by addition of 2 U RNase H (BRL) followed by incubation at 42° C. for 20 min. Second strand synthesis was by the same reverse transcriptase involved in first strand synthesis; although reverse transcriptase activity decreases over time, enough residual activity remained to perform second strand systhesis. Second strand synthesis was initiated by the addition of second strand synthesis primer (oligo 2 (SEQ ID NO:2)) to 500 nM final concentration, followed by incubation at 42° C. for 20 min. Oligo 1 (SEQ ID NO:1) was then destroyed by the addition of 2.5 ng Uracil DNA Glycosylase (UDG, BRL) with incubation at 42° C. for 10 min. Subsequent amplification was performed using oligo 2 (SEQ ID NO:2) and oligo 3 (SEQ ID NO:3).

Amplification: The polymerase chain reaction (PCR) was performed using a Perkin-Elmer Thermocycler and Taq DNA polymerase (Perkin-Elmer Cetus) according to protocols supplied by the manufacturer. Specifically, the thermocycler profile was as follows:

| | | |
|---|---|---|
| Time delay: | 10' | 94 C. |
| Denature: | 1' | 94 C. |
| Anneal: | 2' | 55 C. |
| Extend: | 2' | 72 C. |
| Soak: | | 4 C. |

Analysis: Products were analyzed by 2% agarose gel electrophoresis on a Horizon ™ 58 mini-gel apparatus (BRL) at 130 V (16 V/cm) using a cooling fan, followed by ethidium bromide (500 ng/ml) (EtBr) staining and ultraviolet visualization. Agarose gels were blotted to Biodyne B charged nylon (Pall) according to the manufacturer. The PCR products were then detected by hybridization using a $^{32}$P 5'-end labelled oligonucleotide probe (30-mer, $1.8 \times 10^8$ dpm/$\mu$g) at 45° C. at $4 \times 10^6$ dpm/ml. The hybridization buffer contained 5% sodium dodecyl sulfate (SDS), 1.0M NaCl, 30% formamide, 1 mM disodium ethylene diaminetetraacetic acid (Na$_2$EDTA), 50 mM NaH$_2$PO$_4$, pH 7.4, 0.5% gelatin and 100 $\mu$g/ml tRNA. Hybridization reactions were performed overnight and then washed in 0.1×SSC (SSC: standard saline citrate: 150 mM NaCl, 15 mM trisodium citrate, pH 7.0) containing 0.1% SDS at 45° C.

Results: Results were obtained from two different experiments, represented as Experiments 1 and 2.

In Experiment 1, two levels (500 nM and 100 nM) of Oligo 1 (SEQ ID NO:1)) were examined in an installation-amplification sequence. Four different analyte conditions were examined: including $10^5$ molecules of RNA, including $10^5$ molecules of denatured DNA (d-DNA), including $10^5$ molecules of native DNA (n-DNA), and a "No Analyte" control. The DNA analytes were the same templates used to generate the RNA. DNA was denatured by boiling at 100° C. for 5 min in TE buffer. After amplification and EtBr detection as described in Methods, only RNA showed an amplification product. This sole product was of the size predicted from the target sequence and the priming sites chosen. DNA samples and "No Analyte" controls gave no signal by EtBr staining. RNA primed with oligo 1 (SEQ ID NO:1) at 500 nM gave significantly better amplification than did oligo 1 (SEQ ID NO:1) at 100 nM.

In Experiment 2, three levels of PCR primers were examined, and the number of amplification cycles set at 25. Controls which omitted Reverse Transcriptase (RT) or RNase H were included. Detection was both by EtBr staining and Southern blotting followed by hybridization. As in experiment 1, selective amplification was observed at all levels. Omission of either RT or RNase H abolished the ability to amplify under the conditions described.

EXAMPLE 2

INSTALLATION OF A DEFINED SEQUENCE

The following experiment illustrates the use of the present invention to install (attach) a short, defined sequence at the 3'-end of a DNA molecule.

Sample Preparation and Amplification

A reaction was assembled containing reaction buffer (20 mM Tris.HCl, pH 8.4 at 22° C., 50 mM KCl, 2.5 mM MgCl$_2$, 100 $\mu$g/ml bovine serum albumin (BSA, from BRL), 1.0 $\mu$M primer oligonucleotide, 1.0 $\mu$M installation oligonucleotide, 200 $\mu$M of each of the four dNTP's (Pharmacia), and 2.5 U of taq DNA polymerase, and either $10^3$ or $10^5$ copies of a linearized pBR322 plasmid containing a clone of intact Human Papilloma Virus 16. Two samples contained no DNA analyte. The samples were overlayed with mineral oil, and placed into a thermocycler heat block. The reactions were cycled to 95° C. for 1 min, 55° C. for 1 min, and then 72° C. for 2 min. This three-temperature profile was performed twice, followed by incubation at 95° C. for about 1 min in order to make the second strand molecule available for annealing to the promoter oligonucleotide. This may be accomplished by other means, such as by treatment with UDG.

After such incubation, 5 $\mu$l of each reaction was removed and placed on ice, and treated with or without 2.5 ng (0.5 $\mu$l, 250 Lindahl units/rag) of uracil DNA glycosylase at 37° C. for 15 min. Samples were then amplified using the LAT amplification system described in in U.S. patent application Ser. No. 07/542,306. Thus, amplification was accomplished by incubating the product of the installation procedure in a reaction mixture which contained 50 mM Tris.HCl (pH 8.3), 175 mM potassium glutamate, 6 mM MgCl$_2$, 8% polyethylene glycol 8000, 0.01% Triton X-100, 1 mM ATP, 1 mM CTP, 1 mM GTP, 1 mM UTP, 0.25 mM dATP, 0.25 mM dCTP, 0.25 mM dGTP, 0.25 mM dTTP, 10 mM dithiothreitol, 2 pmoles Proto-promoter oligonucleotide, 4 pmole cDNA primer, approximately 200 units Superscript ™ Reverse Transcriptase (BRL), 400 units T7 RNA polymerase, 1 unit T4 DNA ligase, RNase H (0.05 units) in a 25 μl volume. Reactions were incubated at 42° C. for 3 hours.

Detection of LAT Products

A 10 μL portion of each LAT reaction was added to 30 μL of glyoxal mix (50% DMSO, 10% glyoxal, 20 mM sodium phosphate, pH 6.8), and incubated for 1 h at 55° C. The glyoxylated samples were transferred in duplicate using a dot-blot apparatus (Bio-Rad) to Hybond nylon membrane (Amersham). The membranes were fixed 1 h at 80° C. in a vacuum oven, then exposed to ultraviolet light at λ=302 nm for 2.5 min.

LAT products were detected by hybridization to a 51-mer oligonucleotide probe which had been 5'-end-labeled with $^{32}$P to $1.8 \times 10^8$ dpm/μg which was specific for either the (+) target strand (RNA) or (−) strand (cDNA).

The hybridization buffer contained 5% sodium dodecyl sulfate (SDS), 30% formamide, 1M NaCl, 50 mM sodium phosphate, pH 7.4, 1 mM ethylenediamine tetraacetic acid (EDTA), 50 μg/ml tRNA and 0.1% gelatin. Prehybridization was for 30 min, and hybridization at 55° C. for 15 h. Two washes were conducted at ambient temperature in 1×SSC (SSC: standard saline citrate: 150 mM NaCl, 15 mM trisodium citrate, pH 7.0), 0.1% SDS, followed by two washes in the same solution at 50° C. Visualization was by auto radiography.

Results

Table I describes results of the LAT amplification reaction as compared to plasmid hybridization standards.

TABLE I

| SAMPLES | UDG | SIGNAL | APPROX. FOLD-AMPLIFICATION |
|---|---|---|---|
| No Analyte | + | − | − |
| 10 molecules | + | − | − |
| $10^3$ molecules | + | ++ | $10^6$ |
| $10^3$ molecules | − | − | − |
| $5 \times 10^4$ molecules | + | +++ | $10^6$ |

Analysis of LAT products against hybridization standards showed about a million-fold amplification, and a requirement for UDG destruction of the dU-containing installation oligonucleotide.

EXAMPLE 3

INSTALLATION OF A DEFINED SEQUENCE AT THE 5' END OF A MOLECULE

A single stranded 296-base long Dra I fragment (SEQ ID NO: 4) of a phagemid, p16SPHWATSON, which contains the entire human pappiloma virus type 16 genome was used as target DNA to illustrate the principles of the present invention. The nucleotide sequence of this target DNA molecule and its flanking sequences are shown below (shown 5'→3'; DraI cleavage recognition sites (TTT AAA) are double-underlined; the 296 base pair region of SEQ ID NO:4 is shown in boldface letters):

```
                10         20         30         40    45   50
  1 AAAAAATACA CTTTTTGGGA AGTAAATTTA AAGGAAAAGT TTTCTGCAGA 65
 51 CCTAGATCAG TTTCCTTTAG GACGCAAATT TTTACTACAA GCAGGATTGA

101 AGGCCAAACC AAAATTTACA TTAGGAAAAC GAAAAGCTAC ACCCACCACC

151 TCATCTACCT CTACAACTGC TAAACGCAAA AAACGTAAGC TGTAAGTATT

201 GTATGTATGT TGAATTAGTG TTGTTTGTTG TGTATATGTT TGTATGTGCT 299
251 TGTATGTGCT TGTAAATATT AAGTTGTATG TGTGTTTGTA TGTATGGTAT 318
301 AATAAACACG TGTGTATGTG TTTTTAAATG CTTGTGTAAC TATTGTGTCA
```

The molecule to be amplified comprises bases 46–314 of this molecule (i.e., a 269 base long molecule). An inverted repeat is introduced to the molecule through the use of an installation oligonucleotide primer having the sequence:

(SEQ ID NO:5)
GCAGACCUAGAUCUGUUUCCACAC-GUGUUUAUU

As will be recognized, this primer was synthesized with dU substituted for dT. For purposes of the present invention, dU is functionally equivalent to dT. The underlined sequence of the installation primer (SEQ ID NO:5, bases 14–33) is identical to bases 46–65 of the target molecule (SEQ ID NO:4), allowing for the substitution of dU for dT. The boldface sequence of the installation primer (SEQ ID NO:5, bases 1–13) is complementary with bases 301–313 (SEQ ID NO:4, bases 301–313) of the target molecule:

Target: .... AATAAACACG TGTGTATGTG TTTTT AAATG ....
Primer         ACACGUGUUUAUU The installation primer is permitted to hybdidize with the target molecule to form a double stranded structure such that the 3' OH terminus of the installation primer may be extended in a template-dependent manner by a polymerase. Such extension results in the formation of nucleic acid molecule whose sequence is complementary to that of bases 1–313 of the target molecule.

As will be recognized, this newly formed nucleic acid molecule will have an inverted repeat comprising the complement of bases 46–65 and the underlined sequence of the installation primer.

The desired nucleic acid molecule can be amplified in accordance with the above-discussed methods of the invention using a single primer ("amplification primer") having the sequence of bases 46–65 of the target molecule (SEQ ID NO:4).

The details of this amplification are as follows: In a 50 μl reaction 100 fg of target DNA was mixed with installation and amplification oligonucleotides (1 μM final concentration). The amplification reaction also contained 25 mM Tris-HCl (pH 8.3), 50 mM NaCl, 1.25 mMMgCl₂, 0.01% gelatin and 200 μM of each deoxynucleotide. Then 2.5 units of Taq DNA polymerase (Perkin Elmer—Cetus) were added to the reaction mix, which was heated to 94° C. for 5 min. The inverted repeat installation primer discussed above was allowed to anneal to target DNA at 55° C. for 10 min followed by 5 min at 72° C. for DNA polymerization.

This denaturation—annealing—extension was repeated to allow the amplification oligo to copy the DNA strand with the inverted repeat. The excess inverted repeat installation oligo was digested by addition of 10 ng of uracil DNA glycosylase (UDG) and incubation at 37° C. for 15 min. This was then followed by 30 cycles of amplification as follows: 94° C. (1 min), 55° C. (2 min) and 72° (2 min).

Ten percent of the reaction mix was analyzed by electrophoresis using a 2% agarose gel in which DNA was visualized after staining with ethidium bromide. Significant amplification of target DNA was observed. No visible amplification was observed when one of the following components was not present in the reaction: amplification oligo, inverted repeat installation oligo, or target DNA. In a control reaction, where the inverted repeat installation oligo was predigested with UDG prior to addition to the reaction, no amplification was observed.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for selectively amplifying the concentration of a desired DNA molecule corresponding to a nucleotide sequence of an RNA molecule present in a sample, comprising:
    (a) annealing to said RNA molecule, said molecule having a 5' sequence whose amplification is desired, and a 3' sequence, a primer molecule (I); said primer molecule (I) having a first region whose sequence is complementary to a sequence of said 3' sequence of said RNA molecule, and a second region, 5' to said first region, whose sequence is not complementary to any sequence of said 3' sequence of said RNA molecule, wherein said first region of said primer molecule (I) contains at least one deoxyuridine residue;
    (b) extending said primer molecule (I) to thereby synthesize a first DNA molecule having a sequence complementary to said 5' sequence, said sequence whose amplification is desired, and said 3' sequence of said RNA molecule, and additionally containing said second region of said primer;
    (c) eliminating said RNA molecule from the sample;
    (d) producing a complement of said first DNA molecule using at least one primer (II) having a sequence similar to said 5' sequence of said RNA molecule, to thereby produce a second DNA molecule complementary to said first DNA molecule;
    (e) treating said first DNA molecule with UDG under conditions sufficient to eliminate said deoxyuridine residue contained therein; and
    (f) amplifying the concentration of said desired DNA molecule using at least one primer (III) having a sequence similar to said second region of said primer (I), to copy said second DNA molecule.

2. The method of claim 1, wherein, in step (c), said RNA molecule is eliminated by enzymatic digestion.

3. The method of claim 1, wherein, in step (b) said first DNA molecule is synthesized using an enzyme selected from the group consisting of RNase H− reverse transcriptase, RNase H+ reverse transcriptase, and DNA polymerase.

4. The method of claim 3, wherein said first DNA molecule is synthesized using a DNA polymerase, said polymerase being a thermostable DNA polymerase.

5. The method of claim 4, wherein said thermostable DNA polymerase is taq polymerase.

6. The method of claim 1, wherein said primer (I) has a sequence at or near its 3' end of $[dU]_n$, where n is greater than about 3.

7. The method of claim 1, wherein said primer (I) has a sequence at or near its 3' end of $[dU]_n dX$, where n is greater than about 2, and dX is either dG, dC, or dA.

8. A method for adding a deoxyuridine-containing sequence to a desired nucleic acid sequence, such that said deoxyuridine-containing sequence is located 3' to said desired sequence, wherein said method comprises the steps:
    a) annealing to a first nucleic acid molecule having a sequence complementary to said desired sequence and an additional sequence located 3' thereto, a primer molecule (I), said primer molecule (I) having a first region whose sequence is complementary to a sequence of said additional sequence of said first nucleic acid molecule, and a second region, 5' to said first region, whose sequence is not complementary to any of said first nucleic acid molecule, wherein a region of said primer molecule (I) contains at least one deoxyuridine residue; and b) extending said primer molecule (I) to thereby synthesize said desired DNA molecule containing said deoxyuridine-containing sequence.

9. The method of claim 8, wherein only said first region of said primer molecule (I) contains at least one deoxyuridine residue.

10. The method of claim 8, wherein only said second region of said primer molecule (I) contains at least one deoxyuridine residue.

11. The method of claim 8, wherein both said first and said second regions of said primer molecule (I) contain at least one deoxyuridine residue.

12. The method of claim 8, wherein a complement of said first DNA molecule is formed, and then treated under conditions sufficient to remove said deoxyuridine of said DNA molecule.

13. The method of claim 8, wherein both of said regions of said primer molecule (I) contain at least one deoxyuridine residue, and wherein a complement of said first DNA molecule is formed, and then treated under conditions sufficient to remove said deoxyuridine of said DNA molecule.

14. A kit for preparing a nucleic acid molecule containing:
 a first container containing an oligonucleotide containing at least one dU residue;
 a second container containing an enzyme capable of degrading an oligonucleotide which contains said dU residue.

15. The kit of claim 14, wherein said enzyme is UDG.

16. The kit of claim 14, which additionally contains an enzyme having ribonuclease H activity.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Human papillomavirus
    ( B ) STRAIN: Type 16

( v i i ) IMMEDIATE SOURCE:
    ( B ) CLONE: pT7-13

( x i ) SEQUENCE DESCRIPTION: SEQ ID NO:1:

GGGAGACCGG AAUUCUCCUU CAAUUGCUGA UGCAGGUGAC                    4 0

( 2 ) INFORMATION FOR SEQ ID NO:2:

( i ) SEQUENCE CHARACTERISTICS:
    ( A ) LENGTH: 24 base pairs
    ( B ) TYPE: nucleic acid
    ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Human papillomavirus
    ( B ) STRAIN: Type 16

( v i i ) IMMEDIATE SOURCE:
    ( B ) CLONE: pT7-13

( x i ) SEQUENCE DESCRIPTION: SEQ ID NO:2:

CTGCATGATA ATATATGTTT GTGC             24

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human papillomavirus
        ( B ) STRAIN: Type 16

( v i i ) IMMEDIATE SOURCE:
        ( B ) CLONE: pT7-13

( x i ) SEQUENCE DESCRIPTION: SEQ ID NO:3:

GGGAGACCGG AATTCTCC                 18

( 2 ) INFORMATION FOR SEQ ID NO:4:

( i ) SEQUENCE CHARACTERISTICS:
        ( A ) LENGTH: 350 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human papillomavirus
        ( B ) STRAIN: Type 16

( v i i ) IMMEDIATE SOURCE:
        ( B ) CLONE: p165PHWATSON ( i x ) FEATURE:
        ( A ) NAME/KEY: miscfeature
        ( B ) LOCATION: 28..33
        ( D ) OTHER INFORMATION: /product="DRA I restriction
            recognition site"

( i x ) FEATURE:
        ( A ) NAME/KEY: miscfeature
        ( B ) LOCATION: 323..328
        ( D ) OTHER INFORMATION: /product="DRA I restriction
            endonuclease recognition site"

( x i ) SEQUENCE DESCRIPTION: SEQ ID NO:4:

AAAAAATACA CTTTTTGGGA AGTAAATTTA AAGGAAAAGT TTTCTGCAGA CCTAGATCAG     60

| | | | | | | |
|---|---|---|---|---|---|---|
| TTTCCTTTAG | GACGCAAATT | TTTACTACAA | GCAGGATTGA | AGGCCAAACC | AAAATTTACA | 120 |
| TTAGGAAAAC | GAAAAGCTAC | ACCCACCACC | TCATCTACCT | CTACAACTGC | TAAACGCAAA | 180 |
| AAACGTAAGC | TGTAAGTATT | GTATGTATGT | TGAATTAGTG | TTGTTTGTTG | TGTATATGTT | 240 |
| TGTATGTGCT | TGTATGTGCT | TGTAAATATT | AAGTTGTATG | TGTGTTTGTA | TGTATGGTAT | 300 |
| AATAAACACG | TGTGTATGTG | TTTTTAAATG | CTTGTGTAAC | TATTGTGTCA | | 350 |

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human papillomavirus
        ( B ) STRAIN: Type 16

( v i i ) IMMEDIATE SOURCE:
        ( B ) CLONE: p165PHWATSON ( x i ) SEQUENCE DESCRIPTION: SEQ ID NO:5:

| | | | |
|---|---|---|---|
| GCAGACCUAG | AUCUGUUUCC | ACACGUGUUU | AUU | 33 |